United States Patent [19]

Audibert et al.

[11] Patent Number: 4,639,512

[45] Date of Patent: Jan. 27, 1987

[54] CONJUGATES OF HAPTENES AND MURAMYL-PEPTIDES, ENDOWED WITH IMMUNOGENIC ACTIVITY AND COMPOSITIONS CONTAINING THEM

[75] Inventors: Francoise Audibert, Neuilly sur Seine; Claude Carelli, Suresnes; Louis Chedid, Paris; Pierre LeFrancier, Gif sur Yvette; Michel Level; Jean Choay, both of Paris, all of France

[73] Assignee: Agence National de Valorisation de la Recherche, Paris, France

[21] Appl. No.: 474,361

[22] Filed: Mar. 11, 1983

[30] Foreign Application Priority Data

Mar. 15, 1982 [FR] France ................................. 82 04353

[51] Int. Cl.$^4$ ....................... A61K 39/00; A61K 37/00
[52] U.S. Cl. .................................... 530/313; 530/322; 530/300; 514/8; 514/14; 514/53; 514/54; 424/88
[58] Field of Search ............ 260/112.5 R, 121, 112 B, 260/112 R; 424/85, 88, 89, 92; 530/300, 313, 530/322; 514/8, 14, 53, 54

[56] References Cited

U.S. PATENT DOCUMENTS 4,397,844  8/1983  Baschang et al. .................. 424/177

OTHER PUBLICATIONS

Dreesman et al., *Nature*, vol. 295, Jan. 14, 1982, pp. 158–160, "Antibody to Hepatitis B Surface Antigen After a Single Inocculation of Uncoupled Synthetic HBsAg Peptides".

Bahr et al., *Mol. Immunology*, vol. 19(5), pp. 737–745, May 1982, "Analysis of the Antigenic Relationship of Various Derivatives of N-Acetyl-Muramyl-L-Ala-D-isoglutamine (MDP) Using Anti-MDP Antibodies".

Lerner et al., *Proc. Natl. Acad. Sci.*, vol. 78(6), pp. 3403–3407, Jun. 1981, "Chemically Synthesized Peptides Predicted From the Nucleotide Sequence of the Hepatitis B . . . Dane Particles".

Matsuura et al., *Endocrinology*, vol. 104(2), "A Human Chorionic Gonadotropin-Specific Antiserum Against Synthetic Peptide Analogs to the Carboxyl-Terminal Peptide of Its $\beta$-Subunit".

Reichert et al., *Mol. Imm.*, vol. 17(3), Mar. 1980, pp. 357–363, "Synthesis of Conjugates Containing N-Acetylmuramyl-L-Alanyl-D-Isuglutaminyl (MDP) Their Use as Hapten-Carrier Systems".

Arnon et al., *Proc. Natl. Acad. Sci.*, vol. 77, No. 11, Nov. 1980, pp. 6769–6772, "Antiviral Response . . . Peptide".

Mozes et al., *Proc. Natl. Acad. Sci.*, vol. 77(8), Aug. 1980, pp. 4933–4937, "Efficient Genetically Controlled Formation of Antibody to a Synthetic Antigen . . . isogluatamine".

Carelli et al., (including J. Gaillard), *Proc. Natl. Acad. Sci.*, vol. 79(17), pp. 5342–5395, "Immunological Castration of Male Mice by a Totally Synthetic Vaccine Administered in Saline".

Chedid et al., *Infect. Immun.*, vol. 35(2), Feb. 1982, "Biological Activity of a New Synthetic Muramyl Peptide Devoid of Antigenicity".

Primary Examiner—Thomas G. Wiseman
Assistant Examiner—Robin Lyn Teskin
Attorney, Agent, or Firm—Weiser & Stapler

[57] ABSTRACT

The invention relates to an immunogenic principle containing a specific antigen determinant of a predetermined native antigen. This immunogenic principle is constituted by a conjugate between a hapten bearing said antigenic site and a muramyl-peptide, essentially in the absence of supporting macromolecules, this conjugate having an immunogenic effect not only against itself, but also with respect to the native antigen carrying said antigenic site.

25 Claims, No Drawings

CONJUGATES OF HAPTENES AND MURAMYL-PEPTIDES, ENDOWED WITH IMMUNOGENIC ACTIVITY AND COMPOSITIONS CONTAINING THEM

BACKGROUND OF THE INVENTION

The invention relates to a novel category of compounds, derivatives of molecules of small molecular weight and modified by muramyl-peptide derivatives, this modification being adapted to confer on them properties of immunogenicity of which they were essentially devoid before their modification by these muramyl-peptides

DESCRIPTION OF THE PRIOR ART

It is known that the derivatives commonly named "muramyl-peptides" and which include a saccharide unit, particularly of the N-acetyl-muramyl type, and a peptide chain attached to this saccharide unit, are known as possessing immunological adjuvant properties. Numerous representatives of these muramyl-peptides have been described in the technical literature.

The capacity that the muramyl-peptides possess of stimulating the immune response of a host with respect to an antigen enables their application to be contemplated, for example, to vaccinating compositions employing an immunogenic agent, either weak in nature, or weakened, by reason of extensive purification, particularly by reason of the existence of toxicity or of other troublesome side effects in the initial antigen.

To strengthen still further the adjuvant immunological effect of muramyl-peptides, it has also been proposed, particularly in European patent application No. 3833, to fix these muramyl-peptide derivatives to the antigen studied, particularly through covalent bonds, in other words, to "conjugate" them to these antigens. In certain cases, this type of bond enables additional potentiation of the immunogenic effect of the so-modified antigen. It has however been also observed that this conjugation could be accompanied by pyrogenic properties and separate immunogenic reactions, more particularly directed against the muramyl-peptide derivative itself. This is, by way of example, what is observed with conjugates formed between the tetanus toxin and muramyl-peptide derivatives.

In parallel with these techniques, novel types of immunogenic agents have developed which consist of conjugation products between a fragment possessing the structure of a portion of a natural or "native" antigen and a carrier molecule, particularly a natural or synthetic macromolecule. For example, the fragment consists of a peptide possessing a sequence also present in a native peptide antigen. However, with the exception of some peptides which already possess themselves a number of amino acids sufficient to confer on them an extremely weak, but detectable immunogenic activity, the immunogenicity of these fragments is in general subject to their conjugation with the above-said support.

Reference is made, for example, to the following recent publications which describe such immunogenic principles:

AUDIBERT, JOLIVET, CHEDID, ALOUF, BOQUET, RIVAILLE and SIFFERT, "Nature", Vol. 289, No. 5798, p. 593-594, Feb. 12, 1981, MOZES, SELA and CHEDID, "Proc. Natl. Acad. Sci. USA", vol. 77, No. 8, p. 4933-4937, August 1980, ARNON, SELA, PARANT and CHEDID, "Proc. Natl. Acad. Sci. USA", vol. 77, No. 11, p. 6769-6772, November 1980, LERNER, GREEN, ALEXANDER, LIU, SUTCLIFFE and SHINNICK, "Proc. Natl. Acad. Sci. USA", vol. 78, No. 6, p. 3403-3407, June 1981, ARNON, MARON, SELA and ANFINSEN, "Proc. Natl. Acad. Sci. USA", vol. 68, No. 7, p. 1450-1455, July 1981, and SHUJI MATSUURA, MASANOBU OHASHI, HAO-CHIA CHEN and Gary D. HODGEN, "Endocrinology", vol. 104, No. 2, 1979.

Certain authors have already tested the capacity of certain peptides of inducing the production of antibodies in the absence of any prior coupling with a support macromolecule. For example, R. A. LERNER et al in the document already mentioned and G. R. DREESMAN ("Nature", vol. 295, of Jan. 14, 1982, p. 158-160) observed that certain peptides having sequences in common with the HBsAg antigen have led to the production of antibodies detectable in the mouse. According to DREESMAN, the association of these peptides with an adjuvant, more particularly the complete Freund antigen (FCA), an alum, liposomes, with which had possibly been incorporated the N-acetyl-muramyl-L-alanyl-D-isoglutamine (MDP) has not had the effect of significantly increasing the primary immunitary response induced by peptides of the type concerned.

GENERAL DESCRIPTION OF THE INVENTION

The invention arises from the discovery that the coupling, essentially in the absence of a carrier macromolecule, to a haptene or haptenic fragment of low molecular weight possessing at least one "antigenic site" by covalent linkage of the MDP or of analogs, homologs or derivatives of the latter, particularly of all muramyl-peptide derivatives or analogs known to possess adjuvant properties of the immune response with regard to antigens, resulted in immunogenic compounds having an unexpected in vivo immunogenic effectiveness.

These immunogens have in addition the unexpected property of being practically or entirely devoid of an in vivo pyrogenic effect, contrary to the conjugates previously described between MDP and antigens of high molecular weight (the latter consisting of a natural antigen or of a conjugate of a molecule, particularly a peptide bearing an antigenic site, to a supporting macromolecule). This absence of in vivo pyrogenic action is observed both for derivatives or analogues of MDP which are pyrogenic when they are administered alone and whose pyrogenicity diminishes, even disappears after coupling with the hapten, and for derivatives or analogues of MDP which are without pyrogenic action when they are administered alone and whose apyrogenicity is maintained after conjugation.

The invention relates more particularly to hapten muramylpeptide conjugates which do not induce the production of antibodies directed against the muramyl-peptide part of the conjugate.

In the foregoing, the term "hapten" has been given a very wide meaning. It signifies any hapten or haptenic fragment of low molecular weight, whatever its method of production, whether it be by fractionation, depolymerisation, synthesis or genetic recombination.

Also in the foregoing, the expression "antigenic site" means any configuration, particularly surface configuration of the hapten recognisable by a previously formed antibody with respect to an antigen having a site in common with this hapten. The hapten whose conformation may be modified by conjugation to the MDP type product, according to the invention, induces in vivo antibodies or a specific cell-mediated reaction not only against itself, but in addition—in the case where the hapten has a structural element in common with a native antigen—against the native antigen itself or the antigen which may possibly be formed by coupling of the hapten with a macromolecular support. For example, a hapten consisting of a sequence comprising a small number of amino acids is, when it is coupled to a muramyl-peptide, capable of inducing in vivo antibody formation active against the polypeptide or the antigenic protein having in common with the hapten the same amino acid sequence.

This applies also in a same manner to haptens which are not exclusively peptidic. In this respect, the hapten consists, for example, of an oside structure of low molecular weight, which can be constituted by a monosaccharide or several monosaccharides connected to one another for example by a glycoside type linkage. These oligosaccharides may be either linear, or branched. They may belong to the family of hexoses or of pentoses; they may be neutral or aminated, include uronic acid- or sialic acid-units. They may carry substituents usually contained in natural structures, such as acetyl, sulphate or phosphate. These indications are given by way of example but are not limiting and generally all peptidic and/osidic haptenes are included which include structure elements which are equivalents to structural elements contained in an antigen of higher molecular weight, whether this hapten is included in the chain or is located at a terminal position.

The invention relates more particularly to the conjugates of muramyl-peptide and hapten belonging to the categories already mentioned above which, when they are administered in vivo, induce an immune reaction (production of antibodies or cell-mediated reaction with respect to the native antigen containing a structural element present in the hapten of the type concerned. It is understood that, when in the following reference is made to the capacity of the haptens according to the invention to induce the production of antibodies, it amounts to a simplification of language of which the nature is not limiting. It is naturally to be understood that, generally, this expression will encompass any immune reaction, including here cell-mediated reactions.

Generally, the haptens employable for the constitution of the conjugates according to the invention have structural elements in common under the conditions stated above, with any type of known antigen or utilisable as a vaccinating principle. By way of example of the antigens concerned will be mentioned active principles extracted from infectious microorganisms or the infectious microorganisms themselves (attenuated or killed vaccines). More particularly haptens capable of being employed within the scope of the invention may have structural elements present in constituents of these pathogenic agents (such as bacteria, parasitic viruses, rickettsias, protozoas, etc.). By way of example may be mentioned the haptens having structural elements in common with antigenic proteins belonging to the envelopes of the viruses of B viral hepatitis, influenza, herpes viruses, or again proteins of bacterial walls, for example, streptococcal, etc. As haptens having structural elements in common with antigens not exclusively peptidic or non peptidic, may be mentioned oligosaccharides, glycopeptides, lipopeptides, glycolipids, lipids, steroids, etc. More generally, reference may also be made to the information provided in European patent application No. 3833.

The invention extends also particularly to the haptenes or haptenic fragments of low molecular weight which may be obtained synthetically.

The invention also relates to conjugates of muramyl-peptides and other molecules or fragments of molecules, such as hormones, particularly peptide hormones, for example hormones capable of regulating blood pressure or regulating activities of the various endocrine glands, such as the hypophysis, sexual glands, etc., or steroid hormones, or neuromediators, including neuropeptides, or of tissular antigen determinants, for example antigenic determinants of blood groups, or lymphokines, or cellular receptors, etc., which are naturally present in living organisms and immunologically tolerated by the latter.

The invention hence is more particularly concerned with the conjugates of such particular molecules or molecule fragments with MDP derivatives, whereby the immunogenic properties acquired by the conjugates obtained enable them to induce modification in the immune behaviour of the organisms to which these molecules are administered, more particularly to promote in these organisms the production of antibodies active against said particular molecules or molecular fragments themselves. The particular molecules or molecule fragments may consist of natural molecules or be derived from natural molecules. It is known that there are domains where such modification is sought, for example at the level of hormones intervening in the reproduction of living species. In this respect, the invention applies to modified hormones which may possibly be used as contraceptive means.

The process also permits the production of selective immunological hypophysectomy, leaving intact hypophysial hormones having considerable importance for the vital functions of the organisms, such as growth hormone, ACTH, TSH, as well as the hormones of the post-hypophysis. The use of this selective and non surgical hypophysectomy may have important clinical indications, particularly in the case of certain dependent hypophysial or gonadotrophic hormone tumors.

The invention is concerned more immediately still with hormones modified according to the invention, useful as veterinary vaccines enabling an increase in meat production by immunological castration.

The interest of the process resides also in that the dependent hormones of LH—RH are important for the proper development of the animal and its weight increase up to several months (6 to 9 months), an age at which it is no longer possible to practice to effect surgical castration, which in fact is usually practised before 3 months. Immunological castration would enable the secretion of hypophysial hormones to be stopped at the most favorable time for meat production and without using drastic methods.

The invention relates consequently to conjugates of haptens and muramyl-peptides, in which the hapten portion has a sufficiently low molecular weight to cancel the pyrogenic action which is observable on the occasion of the coupling of the same muramyl-peptides to antigens of higher molecular weight. The hapten portion must in addition still have a sufficiently low molecular weight for the conjugate obtained not to be liable to induce in addition to the expected immunogenicity, the production of antibodies directed against the muramyl-peptide portion itself of the conjugate.

In particular, the invention relates to conjugates of muramyl-peptides and haptens whose molecular weights do not exceed about 5,000 and advantageously are less than 3,000. In advantageous cases, the molecular weights of the immunogenic and apyrogenic conjugates are at the most of the order of 2,000. It may be observed that, apart from some notable exceptions (particularly LH—RH), the haptens coming within the category with which the invention is concerned are, in the unconjugated state, devoid of detectable immunogenicity, and this even in association with MDP.

The haptenes with which the invention is concerned may also be defined as consisting of those which have a sufficiently low molecular weight for the conjugates which they are capable of forming with MDP, not to result in a pyrogenic reaction exceeding the induction of an increase in temperature of 0.6° C., when they are administered intraveneously to rabbits, at dosage rates which can reach 100 micrograms per kilo, even 300 and even 500 micrograms of conjugate per kilo.

When peptides, synthetic or not, are concerned, the haptens brought into play in the invention comprise preferably less than 50 aminoacyl residues (excluding the C-terminal eicosapeptide of β-hCG), particularly less than 30, preferably less than 20 aminoacyls, advantageously less than 50 aminoacyls. The invention may again bring into play oligomerised haptens, inasmuch as the oligomers meet the other conditions mentioned above, as regards the haptenes conjugatable to form immunogens.

By way of example of haptens utilisable for the manufacture of the conjugates according to the invention, may be mentioned in the first place hormones, particularly of the category of peptide or glycopeptide hormones. Among the latter, may be mentioned the luteotropin release factor, known under the designation LH—RH, peptide fragments, or synthetic peptides endowed with similar properties, for example decapeptides of the type Glu—His—Trp—Ser—Tyr—Gly—Leu—Arg—Pro—Gly—NH$_2$ or the corresponding free acid pGlu—His—Trp—Ser—Try—Gly—Leu—Arg—Pro—Gly.

In addition may be mentioned more particularly the C-terminal peptide of human chorionic gonadotropin (hCG), excepting the eicosapeptide. By way of example may be mentioned C-terminal peptides of the sub-unit of hCG, particularly a triacontapeptide containing the aminoacyl residues corresponding to those in hCG-β or terminal synthetic derivatives of the type described by S. MATSUURA et al (publication already mentioned above), FSH fragments, etc., or peptides consisting essentially of 109-145 and 111-145 sequences of the C-terminal sub-units of hCH-β described by Arthus C. J. LEE et al in "Molecular Immunology", vol. 17, 0.749-756. Modification of these hormones by coupling with muramyl-peptides results in immunogenic principles capable of inducing in vivo the production of antibodies against the natural hormones concerned, immunogenicity all the more remarkable as the hapten-modified-immunogens so obtained have extremely low molecular weights.

Also to be mentioned are the conjugates bringing into play coupling between a muramyl-peptide and various synthetic peptides having common sequences of aminoacyl-residues with the principal constituent peptides of the HBsAg antigens, such as are identified in the publications already mentioned, particularly those of which the end aminoacyls correspond to those which, in the sequence of HBsAg occupy the following positions: 48–81; 2–16; 22–35; 95–109; 117–137; 122–137; 117–135 (according to the structure given by PASEK et al and reproduced in the article of LERNER). In addition will be mentioned synthetic peptides of the type described by E. H. BEACHEY et al which are capable, when coupled with a muramyl-peptide, of forming antibodies active against the protein M of the surface of *Streptoccocus piogenes*. Reference may also be made to the peptide sequences defined in U.S. Pat. No. 4,284,537, more particularly those defined under the abbreviations CB$_6$ and CB$_7$.

By way of saccharidic or osidic haptenes, may be mentioned, for example, blood groups A and B, polysaccharide C of Streptococcus C, cellobiuronic acid (Pneumo type III), such as described by W. F. GOEBEL, "J. Exp. Medicine", 1939, p. 353–363.

Reference will also be made with advantage, as regards the various hapten types capable of being brought into play in the coupling according to the invention, to the peptide sequences described by Thomas P. HOPP et al in "Proc. Natl. Acad. Sci. USA", vol. 78, No. 6, p. 3824–3828, in which have passed under review other peptide sequences capable of being rendered antigenic by coupling with supporting macromolecules, but which, within the scope of the present invention, may also be rendered immunogenic by coupling with a muramyl-peptide derivative.

Of course, the various peptides and other haptene types envisaged in the literature and which, in this respect, may be used to constitute the immunogen agents such as defined in the present patent application, only constitute examples of the various haptens which can be employed. It is self-evident that haptens corresponding to the conditions of the invention and corresponding to a predetermined antigen are not always immediately available. When the constitution of the antigen is or can be known, particularly when the latter consist of a polypeptide of which the sequence is known or can be determined, it will be up to the specialist to seek those elements of the structure of this antigen which would be capable of bearing an immunogenic site under the conditions which have been indicated above. Several approaches with respect to this question have already been the subject of prior publications. To recall this, may be mentioned for example the articles of LERNER and HOPP mentioned above, in which investigation methods are proposed enabling marking of the sequences contained in an antigen of peptide structure and capable of bearing an immunogenic site, the sequences concerned being then synthesisable and testable particularly conveniently when recourse is had to the technique of the invention, that is to say by coupling with a muramyl-peptide, for their immunogenic capacity and more particularly their capacity of inducing the production in vivo of antibodies active against the native antigen.

The haptens in the conjugates according to the invention may be coupled to any muramyl-peptide derivatives having immunological adjuvant properties.

The muramyl-peptide portion conjugated to the hapten is advantageously derived from the muramyl-peptide which corresponds to the general formula (I)

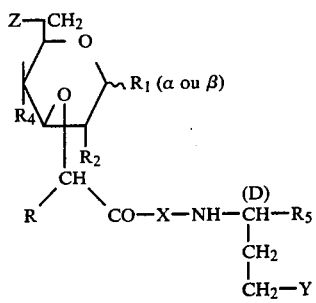

(I)

in which (unless the group concerned is covalently linked to the haptene):

$R_5$ is a free carboxyl group or amido group, or a carboxyl group esterified by an aliphatic alcohol possessing from 1 to 10 carbon atoms, or a carboxyl group substituted by an amino-acid possessing itself a free carboxyl group or an amidated group or a carboxyl group esterified by an aliphatic alcohol prossessing from 1 to 10 carbon atoms.

R is hydrogen or a methyl group $R_2$ is an acetamido or a glycolyl-amido group, $R_1$ is either $-NH_2$, or OH, or a radical comprising at the most 10 carbon atoms, corresponding to an alkyl, aryl, arylalkyl or alkylaryl group, bearing as the case may be hydroxyl, amidocarboxyamid-, sulfonamido-, ether-, thioether-, ester or thioester substituents, $R_4$ is a hydroxyl or an oxyacyl group comprising from 1 to 4 carbon atoms, particularly an oxyacetyl group, X is an aminoacyl residue of the group comprising: alanyl, arginyl, asparagyl, aspartyl, cysteinyl, glutaminyl, glutamyl, glycyl, histidyl, hydroxyprolyl, isoleucyl, leucyl, lysyl, methionyl, phenylalanyl, prolyl, seryl, threonyl, tryptophanyl, tyrosyl, valyl and aminobutyryl, Z is a group substituting the position at C-6 of muramic acid, which correspond to following general formula (II):

$$-R_6-(R_7)_x \quad (II)$$

in which x=0 or 1 and in which
if X=0,
$R_6$ is hydroxyl or amino and if X=1,
$R_6$ hydroxyl group or amino, carboxamido, sulfonamide ether or thioether, ester or thioester,
$R_7$ then being a chain of $-CH_2-$, $-CH=CH-$, $-S-$, $-CO-$ or NH groups, $-CH_2-$; $-CH=CH-$, or NH-groups, said groups being possibly replaced or substituted by aryl groups, preferably phenyl, or heterocyclic as defined below, or again be substituted by carboxylic, amino, sulfhydryl or hydroxyl groups, or by alkyl groups which can include up to 5 carbon atoms or alkylaryl groups, arylalkyl including in all up to 8 carbon atoms or by heterocylic groups including up to six carbon atoms and one or two oxygen, nitrogen or sulfur atoms, the alkylaryl or arylalkyl groups groups mentioned above being able to contain carbonyl groups or again be substituted by carboxyl, amino, sulfhydryl or hydroxyl groups, whereby the above heterocyclic groups may themselves be substituted by alkyl groups which can contain up to 5 carbon atoms, carboxyl, amino, sulfhydryl or hydroxyl, the above said $R_7$ group having none the less a length not exceeding that of an n-decyl hydrocarbon chain.

Y is a free or amidated carboxyl group, or an ester group comprising up to 10 carbon atoms, or substituted by an amino acid, preferably a trifunctional amino acid, that is to say including, in addition to a carboxyl group and an amino group an additional carboxyl amino or hydroxyl group, said trifunctional aminoacid consisting preferably of lysine, ornithine, glutamic acid, aspartic acid or tyrosine: or Y is a group which corresponds to the general formula III:

$$-R_8-(R_9)_x \quad III$$

in which X equals 0 or 1 and
in which $R_8$ is an amide or ester linkage when x is equal to zero, or when x is different from zero, $R_8$ is a carboxamido-, ester- or thioester-group, $R_9$ then having the same meaning as $R_7$.

A preferred class of muramyl-peptides corresponding to the above said general formula consists of those in which X is a glycyl, seryl, valyl, leucyl, aminobutyryl residue, or more preferably again alanyl.

All these aminoacyl groups are preferably (with the exception of glycine) levogyratory aminoacyl groups.

In each of the foregoing classes, preferred subclasses correspond to the above said formula, however with x being equal to zero, in which case Z is advantageously a hydroxyl or amine function.

In each of the previously defined classes, another preferred sub-class corresponds to the formula (I) mentioned above, in which:

x=1, $R_6$ is a carboxamide linkage or sulfonamide ether or thioether, ester or thioester, and $R_7$ represents one of the groups such as those indicated below:

$(CH_2)_n-COOH$, particularly with n=1, 2, 3, or 4
$(CH_2)_n-NH_2$; particularly with N=1, 2, 3 or 4

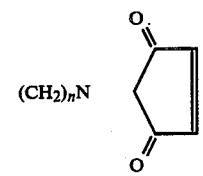

particularly with n=1, 2, 3 or 4
$(CH_2)_n-C_6H_5-NH_2$, particularly with n=0 or 1
$(CH_2)_n-SH$, particularly n=2

The invention relates again to the conjugates derived from muramyl-peptides belonging to any one of the classes and sub-classes mentioned above in which the $R_5$ group is a carboxyl function esterified by n-butyl alcohol, and preferably again those in which simultaneously Y is a $CONH_2$ group The invention relates also, within each of the classes and sub-classes mentioned above, to the preferred categories of haptene-muramyl-peptide conjugates, in which the R group of the muramyl-peptide group is a methyl group.

The invention relates again, within each of the classes, sub-classes and categories as mentioned above, to those, preferred, ones, in which the $R_5$ group of the muramyl-peptide portion of the conjugate according to the invention is an ester group including 1 to 5 carbon atoms.

The invention relates again, within the classes, subclasses and categories mentioned above, to a sub-category of conjugates in which the Z group of the muramyl-peptide portion is a succinyl group.

The invention relates also, within each of the classes, sub-classes, categories and sub-categories mentioned above, to another sub-category of conjugates in which the muramyl-peptide portion of the conjugates concerned, $R_1$ and $R_4$ are simultaneously hydroxyls and $R_2$ an acetamido group.

Other preferred sub-categories of conjugates according to the invention, respectively in the above mentioned classes, sub-classes and categories, contain a muramyl-peptide portion in which simultaneously Z, $R_1$ and $R_4$ are hydroxyls, $R_2$ is an acetamido group, $R_4$ is a methyl group, X is an alanyl group, $R_5$ is a carboxamide group or alternatively an ester group containing from 1 to 5 carbon atoms, and Y has a carboxamide function.

Conjugates also preferred according to the invention are those which contain a muramyl-peptide portion derived from MDP, from α-nbutyl-ester of N-acetyl-muramyl-L-alanyl-D-glutamine or again from 6--succinyl derivatives of the two preceeding muramyl-peptides.

Other preferred muramyl-peptides entering in the composition of the conjugates according to the invention, are mono-α- or γ-esters or diesters of N-acetyl-muramyl-L-alanyl-D-glutamic acid (MDPA), the ester groups containing from 1 to 5 carbon atoms.

In other categories of muramyl-peptides used in the production of preferred conjugates according to the invention, the Y group includes a lysyl group, whereby the other groups are in accordance with those defined in relation to any of the preferred classes or sub-classes defined hereabove. A preferred muramyl-peptide involved in said conjugates consists of N-acetyl-muramyl-L-alanyl-D-isoglutaminyl-L-lysine (MTP).

The invention relates also to a process for manufacturing these conjugates between a hapten and a muramyl-peptide belonging to one of the classes, sub-classes or categories indicated above, this process comprising diverse possible variations.

In accordance with a first technique, recourse may be had to a coupling reaction through glutaraldehyde, to the extend where both the haptene and the muramyl-peptide derivative concerned includes amide functions.

Advantageously, recourse may be had to other forms of coupling which can bring into action predetermined positions on the muramyl-peptide portion. In particular these linkages could come into play at the level either of the $C_6$ position, or that of the $C_1$ of the saccharide ring, or again at the C-terminal end of Y in the peptide chain.

As regards substitutions involving the Z group or the Y group, recourse can be had to coupling methods currently used in peptide synthesis, to the extent where it is possible to form a peptide linkage between suitable functions borne, on the one hand, by the muramyl-peptide and, on the other hand, by the hapten, one bearing, for example, an amine function and the other a carboxyl, hydroxyl or sulfhydryl function or vice versa. Either at the Z group or the Y group shall then carry the suitable terminal function, according as it is desired to effect the fixation at the level of the carbon at the 6 position on the saccharide group, or on the contrary at the level of the end of the peptide chain according to techniques wellknown to the specialist.

It is also possible again to refer to the general techniques contemplated in European patent application No. 3833.

Of course, it is possible to resort to any other type of linkage, bringing into play the combinations which can take place between a sulfhydryl function borne by one of the partners constituted by the hapten and the muramyl-peptide and a maleimide group borne by another reagent, for example by making use of the technique described by T. KITAGAWA and T. AIKAGAWA in "J. Biochem." 79 (1976), 233.

The conjugation can also be effected by using conventional methods of diazotisation or of reaction bringing into play an isothiocyanate, particularly when the muramyl-peptide bears an aromatic amine function (particularly at the level of the groups A or $R_1$), and when the hapten bears an amine function capable of taking part in this reaction. Such techniques of formation are described for example by B. F. ERLANGER in "Pharmacol. Rev.", 25 (1973), 271.

The coupling may also be carried out by the reduction of a Schiff base formed between an aldehyde function borne by one of the reagents and an amine function borne by the other (G. R. GRAY, "Arch. Biochem. Biophys.", 163 (1974), 426).

All these reactions are well known in themselves and the specialist will appreciate that numerous modifications could be introduced to arrive at the same results. As regards moreover more particularly the groups Y and Z, it will be noted also that, between the muramyl-peptide and the hapten, conjugations can be formed by means of bridging, the bridging agent consisting, for example, of a bi-functional reagent. In the event, the bridging group between the muramyl-peptide and the hapten in the final conjugate preferably will not exceed the length of an enchainment corresponding to that of a p-decyl hydrocarbon chain.

Such bridging agent are for example mentioned in paten No. 78 16792 filed June 5, 1978.

In the foregoing, there has especially been mentioned the case of coupling between a muramyl-peptide and a hapten of peptide nature. When the haptene is constituted by an oligosaccharide, the same types of reactions can be employed, as soon as the haptene possesses a free carboxyl function or an amine function, or again an alcohol function which can then form amide or ester bonds with adequate functions borne on the muramyl-peptide.

As a modification, it would also be possible to resort to linking the muramyl-peptide to the $C_1$ position of the oligosaccharide, possessing a reducing terminal sugar, either the pseudoaldehyde function being oxidized into a carboxylic function (G. ASHWELL, "Methods in Enzymol." 28 (1972), 219), or it is used as such (R. GRAY already mentioned). In the first case, a peptide or ester linkage is established; in the second case an alkylamine linkage.

The fixing of the haptene to the muramyl-peptide can take place at several points of the latter, the reverse being also true, so that the invention extends to oligomers of muramyl-peptide and haptene, to the extent that the two constituents have suitable chemical functions, it being understood however that the molecular weight of such conjugates must not normally exceed 5,000.

In general, the haptene constituent and the muramyl-peptide constituent will advantageously be in a ratio by weight comprised between about 1 and 10, particularly between 1.5 and 10, advantageously between 2 and 3.

The invention naturally relates also to compositions prepared in the form of vaccines containing the conjugates according to the invention, in association with a suitable vehicle.

Advantageous pharmaceutical compositions are constituted by solutions, suspensions or injectible liposomes, containing an effective dose of at least one conjugate according to the invention. Preferably, these solutions, suspensions or liposome forms are prepared in an isotonic sterilised aqueuse phase, preferably saline or glucosed.

The invention relates more particularly to such suspensions, solutions or liposome form adapted to be administered by intradermal, intramuscular or sub-cutaneous injections, or again by scarification.

It relates also to pharmaceutical compositions administrable by other routes, particularly orally or rectally, or again in aerosol form intended to come into contact with the mucous membranes, particularly ocular, nasal, pulmonary or vaginal mucous membranes.

In consequence, it relates to pharmaceutical compositions in which one at least of the conjugates according to the invention is found associated with solid or liquid pharmaceutically acceptable excipients, adapted to the constitution or oral, ocular, or nasal forms, or with excipients adapted for the constitution of rectal administration forms or again with gelatinous excipients for vaginal administration. It also relates to isotonic liquid compositions containing one at least of the conjugates according to the invention, adapted for administration to the mucous tissues, particularly ocular or nasal. It relates finally to compositions formed from pharmaceutically acceptable liquified gases, of the "propellent" type, in which the conjugates according to the invention are dissolved or held in suspension, and of which the release causes dispersion in an aerosol.

Advantageously, the vaccinal compositions according to the invention contain in addition a vehicle, such as polyvinyl-pyrrolidone, facilitating the demonstration of the vaccine. In place of polyvinyl-pyrrolidone, it is possible to use any other type of adjuvant in the conventional sense given in the past to this expression, that is to say, a substance enabling easier absorption of a medicament or facilitating its action in the organism. By way of examples of other adjuvants of the latter type, will be mentioned also carboxymethylcellulose, aluminium hydroxides and phosphates or any other adjuvants of this type, wellknown to the technicien skilled in the art.

The pharmaceutical compositions according to the invention are hence essentially intended to induce in the host an immune reaction, enabling it to produce antibodies or a cell-mediated immunity with respect either to the antigen having a sequence in common with the haptene, or to the haptene itself. The last case is of particular interest when the haptene consists of a natural peptide, such as a hormone, whose effects are to be palliated. These pharmaceutical compositions will hence be particularly useful in human or veterinary therapeutics, each time that a modification in the development of the behaviour of the human or animal organism is sought. The development sought may consist of the control or the fertility in animal species or of a controlled orientation of the metabolism of a human or animal host towards suppression of certain hormones. In the latter case, the haptene entering into the conjugate employed will be constituted by the hormone itself or a fragment of the latter.

In the veterinary domain, will be mentioned in addition the increased production of certain constituents at the expense of other constituents. For example, there will be mentioned the applications of veterinary vaccines administered for the purpose of increasing in the animal the production of meat by immunological castration.

The invention relates particularly to haptene conjugates, in which the haptene itself is constituted either by the hormone itself, or by a peptide sequence having a common portion with the hormone, the hormone belonging to the class of peptide or glycopeptide hormones. A particularly interesting hormone in this respect is constituted by the release factor of the luteostimulant hormone LH-RH.

The invention relates also again to biological reagents essentially formed from these haptene antibody conjugates. In particular, the haptene portion will be constituted by an active principle of drug (for example morphine), the biological reagent concerned then being used to manufacture antibodies of reduced apyrogenity, particularly monovalent antibodies, and monoclonal antibodies. These antibodies will then in turn be useful for the constitution of reagents enabling, for example, study of the action of medicaments concerned in the living host. In particular, these antibodies will enable the detection of cell receptors, or again study of the metabolism and of the mode of action of the drugs concerned.

The invention relates again, and this generally, to the antibodies themselves or the preparation of antibodies such as are obtained by administration to a living host of conjugates of haptene and of muramyl-peptides according to the invention. An essential identification characteristic of these antibodies consists naturally in the capacity in that they have of neutralising the conjugates according to the invention and, in addition, when the haptene portion of the latter possesses a structural element common with a native antigen, also the latter.

The invention provides, in particular, as is illustrated below in one of the examples a conjugate of the latter hormone with a muramyl-peptide, having a molecular weight of below 2,000 daltons, having high immunogenicity and at the same time negligible, even non-existent pyrogenic effect, even when the muramyl-peptide entering into the conjugate has itself a certain level of pyrogenicity. In addition, and contrary to what is observed with the conjugates of the state of the art formed against the antigens of higher molecular weight and muramyl-peptides, those of the invention are devoid of immunogenic action with respect to the muramyl-peptide constituent within the limits which can be detected with the detection methods in use at present.

Other characteristics of the invention will appear also in the course of the description which follows of preferred examples of the practising of the invention, as well as of the results which can be achieved by the conjugates according to the invention.

DESCRIPTION OF PREFERRED EMBODIMENTS

I—Synthesis of (LH—RH)—MTP

To obtain a typical conjugation reaction, 3 mg of LH—RH are added in the acid form to 242 mg of N-ethyl-N'(3 methyl-aminopropyl)-carbodiimide hydrochloride (ECDI) and to 43 mg of 1-hydroxy-benzotriazole (HOBT), in 0.4 ml of dimethylformamide (DMF) as solvent. Incubation is carried out with magnetic stirring for 7 hours at ambiant temperature. Then to this solution 3.24 mg of MTP (N-acetyl-muramyl-L-alanine-D-isoglutaminyl-L-Lysine) mixed with 0.3 ml of distilled water is added and the reaction is allowed to continue with magnetic stirring for 48 hours at ambiant temperature. The products of the reaction are taken up in a 0.15M MaCl solution and the conjugates formed are recovered by fractionating on a molecular sieve of SEPHADEX G10. The conjugates are eluted in the dead volume. The contents of peptides and of muramic acid are evaluated by the method of Reissig et al, J. Biol.Chem. 217,959–966 (1956). It is found that 93% of MTP is coupled: thus the number of MTP molecules per molecule of LH—RH approaches 1:1.

Synthesis of the conjugate MDP-tetanus toxin (manufactured as control)

To 16 mg of MTP, is added 0.15 mg of DMF plus 0.01 ml of PBS at pH 7.4 (saline solution buffered with phosphate) then 300 μg of ECDI, 1 mg of HOBT and 2 mg of tetanus toxin. The reaction is allowed to continue for 15 minutes with magnetic stirring, at ambiant temperature and the in the dark; then to this mixture 300 μg of ECDI is added, 1 mg of HOBT of 2 mg of tetanus toxin; the reaction is continued further for 15 minutes and the same operation is repeated 9 times. It is then observed that 20 mg of tetanus toxin have been used. At the end of the reaction the conjugate is recovered by chromatography of SEPHADEX G75 column in PBS. The conjugate is contained in the first elution peak. The respective determinations of tetanus toxins and of MTP are carried out by the method of Folin and Reissig.

Coupling of MTP to fresh erythrocytes

The coupling of MTP to fresh erythrocytes by means of benzoquinone, is carried out by employing the following process: 0.2 ml of benzoquinone (30 mg/ml) is added to 3 mg of MTP dissolved in 0.2 ml of 0.2M PBS at pH 7. The reaction is allowed to continue for 90 minutes at ambiant temperature, in the dark, with stirring. The reaction is stopped by chromatography on a column of SEPHADEX G25 molecular sieve in an 0.1M NaHCO$_3$ medium at pH 8.0. The MTP activated by the benzoquinone, is eluted in the dead volume. It is added to 0.8 ml of a suspension of 50% of sheeps fresh red blood cells in a 0.1M NaHCO$_3$ solution. The mixture is allowed to incubate overnight at room temperature with stirring, then the red blood cells retaining the MTP with the PBS are washed three times.

Immunisation by LH—RH coupled to the muramyl-peptide and administered in a saline solution or in an incomplete Freund adjuvant (FIA)

A volume of 0.1 ml of the following solution is administered by sub-cutaneous injection and at days 0, 2, 4 and 29 to several groups of Swiss male mice, aged 6 weeks.

(1) 50 μg of LH—RH emulsified in Freund complete adjuvant
(2) 50 μg of LH—RH emulsified in FIA
(3) 8.6 μg of LH—RH conjugated with 4.3 μg of MDP and emulsified in FIA
(4) 50 μg of LH—RH in PBS
(5) 8.6 μg of LH—RH conjugated with 4.3 μg of MDP in PBS.

Into three additional control groups were injected, either FCA, or FIA, or PBS, with neither antigen nor MDP.

It should be noted that before use, the antigen (LH—RH pure or coupled) was absorbed on 50% PVP (polyvinylpyrrolidone) in 0.9% of NaCl and that incubation was continued for 2 hours; then the mixtures were emulsified with FIA or FCA or added to the PBS.

The volume of 0.1 ml injected in the mice subcutaneously contained 12.5% of PVP.

At days 23 and 50, all the mice were bled, sacrificed and their serums collected and combined for each of the groups. Their testicles and seminal vesicles were taken out, weighed, placed in a Boin solution and prepared for histological examination.

Detection of anti-(LH—RH) antibodies

The anti-(LH—RH) antibodies were detected as follows:

50 μl of undiluted serum to be tested, 50 μl of normal rabit serum diluted to 1/80th in PBS and 10 μl of (LH—RH) labelled with iodine 125 (approximately 10,000 desintegrations per minute: dpm) was added. It was left for incubation to continue for 72 hours at 4° C. Then 150 μl of a suspension cooled in ice, of activated charcoal coated with dextran (obtained by adding 250 mg of activated charcoal to 100 ml of a dextran solution in 0.01M PBS) was added. It was left at 4° C. for 5 minutes. After centrifugation at 2500 rpm for 20 minutes the supernatant liquor was decanted and its radioactivity was determined, by the method of HABER et al, "Manual of Clinical Immunology" edited by Rose N. R. & Friedman H. pp 190–196. Preliminary study has indicated that charcoal coated with dextran could absorb up to 95% of pure (LH—RH) under the conditions used.

Detection of anti-MTP antibodies

The presence of anti-MTP antibodies was checked by means of a hemolytic test carried out in microtitration plates provided with U cavities (Cooke Engineering) in the following manner: the serums were decomplemented by inactivation for 30 minutes at 56° C. 50 μl of serum which had undergone double dilution were mixed with 50 μl of PBS. 20 μg of fresh red blood cell-MTP conjugates was added at a concentration of 2.5% and the plates were left to incubate at 37° C. for 15 minutes; finally 20 μl of complement (normal guinea pig serum diluted to 1:20 with PBS) was added and the plates were left again to incubate at 37° C. for 30 minutes, before noting the results.

Evaluation of the pyrogenicity

The tests were carried out on New Zealand rabbits of 2.5 to 2.8 kg. The temperatures were taken with a thermistor probe introduced into the rectum of the rabbits to a length of about 8 cm and connected to a telethermometer (model no.TE3; Ellab, Copenhagen, Danemark). The rabbits were kept and observed in an air-conditioned room at 20° C. Injections were only carried out on those whose temperature remained stable in the course of the preceding 30 minutes. The temperatures were measured for 3 hours after the injection of the compositions whose possible pyrogenicity was under study. The results are expressed by the average variation of temperature (°C.) obtained for the rabbits in the course of the 3 hours which followed the intravenous injection of the composition under study. A minimum pyrogenic dose corresponds to the amount producing an elevation of 0.6° C.

The following results were observed.
(a) Immunisation tests

The results are indicated in table I below. They are expressed as follows: ratio of the number of disintegrations per minute (dpm) of the supernatant to the total number of dpm, and multiplied by 100.

TABLE I

| Treatment | Fixation (in %) |
|---|---|
| LH-RH 50 µg + FCA | 30.5 |
| LH-RH 50 µg + FIA | 2.5 |
| LH-RH 50 µg + PBS | 10 |
| LH-RH)-MTP + PBS | 63 |

In the absence of antigen no fixation was observed in the serums of the controls injected with FAC FIA or PBS (the fixation measured (to the maximum of 2.3%) not being significant). Antibodies are however produced when 50 µg of (LH—RH) are emulsified in FAC (30.5% fixation). No significant response was detected in the group which received 50 µg of (LH—RH) in FIA (fixation 2.5%) and the weak response obtained with PBS (10%) is without significance. A strong response is obtained with serum coming from animals immunised with the conjugate MTP—(LH—RH) although the conjugate contains only 8.6 µg of (LH—RH) and 4.4 µg of MTP. Surprisingly, the antibody responses are even higher when when equal amounts of MTP—(LH—RH) conjugates were administered in an aqueous medium. These results indicate that the MTP—(LH—RH) conjugates, are both more effective than the association of (LH—RH) and FCA, both in FIA and in PBS.

Histological study

The average weight of the testicles was slightly increased (252 mg to 279 mg) following the administration of 5 or 50 µg of (LH—RH) in PBS. Although this increase is significant (p 0.05) it is not accompanied by any histological change. On the contrary, the same amount of antigen administered in FCA produces a substantial increase of the weight of the testicles with a reduction in sperm production and a slight atrophy of the seminiferous tubules in certain cases. On the contrary in the animals which had received the conjugate MTP—(LH—RH) in solution in PBS, the weight of the testicles was distinctly lower (p 0.01) than in the other groups. In addition, histological studies of the testicles have shown only in this group a marked atrophy at the same time of the interstitial and of the seminiferous tubules, which were practicly devoid of germinative cells in 9 mice out of 10.

Measurement of the anti-MTP antibodies

Same combined serums, previously tested for 125 I—LH—RH fixation activity were also studied as regards their content of anti-MTP antibodies by means of a hemolytic test with conjugates of red blood cells and MTP. An anti-MTP rabbit serum, obtained after hyperimmunisation with a conjugate of alphamethylester of MTP and bovine albumin serum, was used as control antigen. Although hemolysis reactions were observed with rabbit anti-MTP serum up to a final dilution of 1:30.720, no anti-MTP antibodies were detected in any of the groups treated with the conjugate MTP—(L-H—RH).

Detection of possible pyrogenicity of the conjugates studied and of conjugates with comparison molecules.

The results are shown on table II which follows. It shows the remarkable absence of pyrogenicity of the conjugates according to the invention, in comparison with the pyrogenicities either of muramyl-peptide itself, when the latter is in the isolated state, or of a conjugate that the same muramyl-peptide can form with a native antigen, such as tetanus toxin. The conjugate according to the invention [(LH—RH)—MTP] does not induce a significant temperature elevation in the animal, even if the relative dose of MTP in the conjugate is of the order of 9.3 µg of MTP. These results are to be compared in particular with those obtained under the same conditions with the comparison conjugate (TT-MTP), which induces a quite considerable rise in temperature, even when the relative proportion of MTP in the conjugate administered is 100 times smaller than that in the invention.

It is moreover to be noted in addition that higher doses of the conjugate (LH—RH)—MTP containing a relative proportion of 77 µg of MTP have no induced a marked temperature rise in the animal.

TABLE II

| Treatment | Dose (µg) | Individual temperature differences (Δt) | Means |
|---|---|---|---|
| PBS control | | 0;0;0.2; 0.1 | 0.1 |
| LH-RH control | 0.86 | 0;0;0.6 | 0.2 |
| | 8.6 | 0.3;0.3;0.5 | 0.4 |
| | 145 | 0;0.1;0.1 | 0.1 |
| Tetanus toxin "T-T" | 100 | 0.5; 0.1 | 0.2 |
| (LH-RH)-MTP | 0.4~0.2 | 0; 0.2 | 0.1 |
| | 1.2~0.6 | 0; 0.2 | 0.1 |
| | 3.4~1.8 | 0.1;0.1;0.6 | 0.2 |
| | 17.2~9.3 | 0.1;0.3;0.7 | 0.4 |
| | 86~46 | 0.3 | 0.3 |
| MTP | 86 | 1.1; 1.3 | 1.2 |
| (T-T)-MTP | 100~0.8 | 1.9; 2.1 | 2 |
| | 100~0.7 | 1.2; 1.5 | 1.4 |

The symbol "N" in the table relates to the coupling in the conjugates tested between the relatives doses of hormone on the one hand, and of either the MDP or tetanus toxin respectively, said doses resulting from the first and second number on a same line under the heading "Dose (µg)" of the table.

II—Description of the preparation of the n-butylester of 6-O-(succinylamidopropyl-2-O-(s-L-fucopyranosyl-3-O-(α-D-galactopyranosyl)-(α-D-galactopyranosyl)-2-acetamido-2-deoxy-3-O(D-2-propionyl-L-alanyl-D-glutamine)-D-glucopyranose of the formula

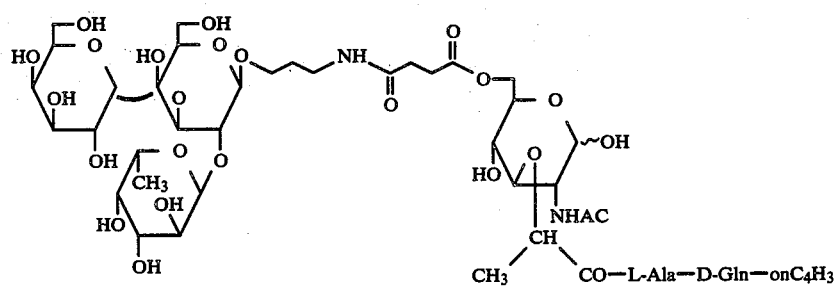

(a) Preparation of 2-allyloxyethyl 2-O-(2,3,4-tri-O-benzyl-α-L-fucopyranosyl)-3-O-(2,3,4,6-tetra-D-benzyl-α-D-galactopyranosyl)-4,6-O-benzylidene-galactopyranoside.

984 mg (0.777 mmole) of 2-hydroxyethyl-2-O-(2,3,4-tri-O-benzyl-α-L-fucopyranosyl)-3-O-(2,3,4,6-tetra-O-benzyl-α-D-galactopyranosyl)-4,6-O-benzylidene-D-galactopyranoside (described in French Patent No.78 10558/2.422.621) were dissolved in anhydrous DMF (15 ml), then sodium hydryde (50% dispersion in oil; 150 mg; 3.1 moles) was added. After 1 hour, allyl bromine was added (0.25 ml; 2.9 mmoles). A further addition of allyl bromide was made after 2 hours (0.25 ml; 2.9 mmoles). After 4 hours, methanol was added (3 ml). The reaction mixture was concnetrated to dryness, taken up again in chloroform which was washed with a saturated sodium chloride solution, with water, then dried over sodium sulfate. After evaporation, the residue was purified by chromatographie on a silica gel column (30 g) in the mixture ethyl acetate-hexane (⅓; v/v).

After evaporation and drying, a white foam was obtained: 745 mg (74.2%) $[\alpha]_D^{20} = +3°$ (c=1, chloroform). The product (I) crystallises in ethanol and melts at 103°-104° C.

(b) Preparation of 3-hydroxypropyl 2-O-(2,3,4-tri-O-benzyl-α-L-fucopyranosyl)-3-O-(2,3,4,6-tetra-O-benzyl-α-D-galactopyranosyl).4,6-O-benzylidene-β-D-galactopyranoside (II)

753 mg (0.58 mmole) of product (I) were dissolved in anhydreous tetrahydrofuran. To this mixture stirred under a current of nitrogen, was added a 0.5M solution of 9-borabicyclo (3.3.1) nonane (1.8 ml; 0.9 mmoles). After 4 hours under reflux, ethanol was added (0.3 ml) then, after 10 minutes, 3M soda (0.4 ml; 1.2 mmoles) and 10M hydrogen peroxide (0.6 ml; 5.8 mmoles). After 1 hour at 50° C., dichloromethane was added (25 ml), then solid potassium carbonate was introduced little by little with stirring, until the solution was clear.

After filtration, evaporation of the solvent and drying, the residue was purified, by chromatography over a silica G column (30 g) in the mixture ethyl acetate-hexane (2/1); v/v): 857 mg (67.3%) $[\alpha]_D^{20} = +1.5°$ (c: 1, chloroform).

(c) Preparation of 3-azidopropyl-2-O-(2,3,4-tri-O-benzyl-β-L-fucopyranosyl)-3-O-(2,3,4,6-tetra-O-benzyl-α-D-galactopyranosyl)-4,6,O-benzylidene-β-D-galactopyranoside (III).

517 mg (0.39 mmole) of product II were dissolved in dry chloroform (10 ml). Triethylamine (0.1 ml; 0.7 mmole), N-dimethyl-aminopyridine (4 mg) and freshly crystallised tosyl chloride (82 mg–0.429 mmole) were added. After 24 hours there were again added triethylamine (0.025 ml) and N-dimethyl-aminopyridine (3 mg) and tosyl chloride (20 mg).

After 24 hours, dichloromethane was added (20 ml) as well as water (5 ml).

After 2 hours stirring, the organic phase was washed with 2M hydrochloric acid, water, sodium bicarbonate in saturated solution and with water.

After drying over sodium sulfate and evaporation, a residue is obtained (558 mg; 96.8%). This product was dissolved in dimethylformamide (15 ml), then sodium azide (76 mg) was added. The reaction mixture was stirred at 80° C. for 2 hours, then concentrated to dryness. The residue obtained was purified on a column of silica G gel (20 g) in ethyl acetatehexane (1/1; v/v: 462 mg (87.8%). The product was crystallised in ether-hexane: m.p. 86°-87° C.; $[\alpha]_D^{20} = +3°$ (c=1, chloroform).

(d) Preparation of 3-aminopropyl 2-O-(α-L-fucopyranosyl)-3-O-(α-D-galactopyranosyl)-β-D-galactopyranoside (IV).

450 mg of product (III) were dissolved in acetic acid (30 ml) then stirred under hydrogen atmosphere, in the presence of 5% palladium on charcoal, for four to five days. The reaction mixture was filtered and the product obtained by lyophilisation (144.5 mg; 69%). $[\alpha]_D^{25} = +5.5°$ (c=2, water).

(e) Preparation of the composition of formula I.

The n-butyl ester of 6-O-succinyl-2-acetamido-2-deoxy-3-O-(D-2-propionyl-L-alanyl-D-glutamine)-D-glucopyranose (6-O-Suc-MDPG-onBu) (181.6 mg; 0.28 mmole) was dissolved in dimethylformamide (6 ml). Hydroxybenzotriazole (48.5 mg; 0.28 mmole and N-cyclohexyl-N' (β.(N-methyl-morpholino)-ethyl)carbodiimide p-toluene sulfonate (118.5 mg; 0.28 mmole) were added.

After one hour, the product of formula (IV) (85 mg; 0.14 mmole) was added in solution in dimethylformamide (3 ml) in the presence of N-methylmorpholine (0.015 ml). After 24 hours, the reaction mixture was concentrated to dryness and desiccated. The residue obtained was purified on a column of ion exchange resin, known under the name AG-50-W-X2 (OH), which was eluted with water. The fractions determined by thin layer chromatography were combined and lyophilised. The product obtained (217 mg) was purified on a column of ion exchange resin known by the name AG-I-X2 (acetate), which was eluted with water. The purified fractions were combined and lyophilised. The product obtained (88 mg) was finally purified on a silica column (lobar column, type A Merck) eluted in the mixture of solvent systems ethyl acetate-pyridine-acetic acid-water (5-5-1-3 and 6-2-O,6-1; v/v). The fractions containing the product I were combined and freeze dried: 47 mg $[\alpha]_D^{23} = +23.1°$ (c=1.03 water).

The estimation of the sugars (galactose and fucose) was done accoding to Z. DISCHE and L. B. SHETTLES, "J. Biol. Chem.", 175 (1948) 595 and that of the amino acids and of the muramic acid by amino acids analysis, after complete acid hydrolysis (6N hydrochloric acid, 110° C., 20 hours) according to S. MOORE and W. H. STEIN, "J. Biol. Chem.", 176 (1948) 367.

The ratio found between the content of amino acids and that of galactose and fucose was 0.95.

The conjugate finally obtained was devoid of pyrogenicity. At a dose of 0.5 mg/kg it only induced an insignificant temperature rise of 0.1° C. in the rabbits.

III—Preparation of a conjugate of MTP and vasopressin.

The starting product was a

[Lys]-vasopressin (LVP) of formula

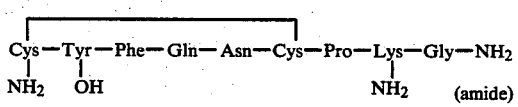

3 chemical groups were available for conjugation (2 amino groups and 1 hydroxyl group).

This compound was subjected to the action of trypsin whereby the resulting compound was obtained:

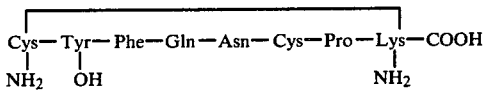

This compound designated as "DesglyLVP" was acetylated to block the amino groups (acetylation by 2.1 molar equivalents of acetic acid per equivalent of DesglyLVP, at pH 7.

The acetylated DesglyLVP was then linked to MTP as follows:

1 mg of acetylated (DesglyLVP) was added to 70 mg of ECDI (molar ratio 1:328) and to 15 mg of HOBT in 0.5 ml of DMF.

The mixture was incubated under magnetic stirring for 7 hours at ambient temperature. 1.32 mg of MTP dissolved in 0.3 ml of distilled water were added to the preceding mixture. The contact was maintained under stirring for 48 hours at ambient temperature to enable the reaction to take place.

The reaction mixture was then filtered and concentrated on a filtration membrane commercialized under the designation AMICON DIAFLO YM2.

After dosage of MTP by the method of Reissig, it was found that 60% of MDP brought into the reaction were conjugated.

The desgly LVP and MTP were found to be in a molecular ratio of approximately 1:1 in the conjugate obtained.

The conjugate of MTP to vasopressin enabled the latter hormons to be injected and did not alter its capability of eliciting antibodies against non-modified vasopressin. Particularly anti-vasopressin antibodies were obtained in the rabbits whose antibodies were found to recognize the N-terminal portion of the non-modified vasopressin.

IV—Preparation of conjugates of MTP and of somatostatin.

The starting somatostatin presented the following formula

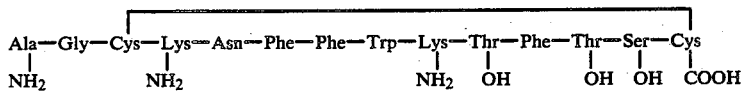

The free amino groups were acetylated by 1.1 molar equivalents of acetic acid at pH 8.2, thereby avoiding the O-acetylation of the free hydroxyl groups of the threonyl and seryl groups, the closest to the C-terminal cyate 1 residue of threonyl and seryl groups. The acetylated somatostatin derivative was conjugated to MTP by the mixed anhydride method disclosed earlier. The conjugation product was separated by filtration on a SEPHADEX GS 15 sieve, both ultrafiltrated and concentrated on an Amicon "DIAFLO" YM2 membrane. The final conjugate contained the somatostatin derivative and the MTP in a weight ratio of about 83.16/32.3. A molecular weight of 2 276 was measured.

The MTP—somatostatin conjugate, when injected in the form of a saline solution into the rabbit, elicited the production of antibodies active against the non-transformed somatostatin.

V—Preparation of conjugates of MTP and of peptides containing the antigenic site of HBs The peptides used can be any of those which have been identified earlier or any ones likely to be synthesized and having a common sequence with the HBs polypeptide.

The reaction can be carried out by using 25 mg of the peptide dissolved in 2.5 ml of a 0.1M sodium bicarbonate solution in admixture with 21 mg of MTP. After 1 hour of contact under stirring at ambient temperature, glutaraldehyde can be added until a 0.1% final solution of the coupling agent is obtained. The conjugate obtained can then be separated by a technique similar to those disclosed in the preceding examples.

As is self-evident and as emerges already from the foregoing, the invention is in no way limited to those of its types of application and embodiments which have been more especially envisaged; it encompasses on the contrary all modifications; it must be appreciated that in all instances where a haptene-muramyl-peptide-conjugate is contemplated in the claims, it should be understood that the significant portion of the muramyl-peptide moiety consists of the basic structure hereafter:

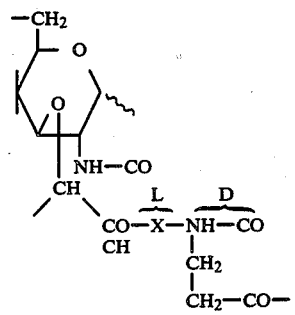

The different derivatives or alternatives which are formed starting from this structure, when completed by substituents such as those defined herein, must be deemed as equivalents of the muramyl-peptide-moieties contemplated in the claims, and as such also protected thereby.

Even more particularly all structural moieties contemplated herein can be considered as alternatives or equivalents of the above defined structure in which X is L-alanyl.

We claim:

1. An immunogenic and apyrogenic conjugate consisting essentially of a hapten covalently linked to a muramyl peptide, which conjugate comprises a molecular weight which does not exceed 5000,
  wherein the hapten is selected from the group consisting of peptides, glycopeptides, oligosaccharides, lipopeptides, glycolipids, lipids and steroids which are incapable of inducing an immunological response in vivo except when bound to an immunological carrier;
  and wherein the muramyl peptide part conjugated to the hapten is derived from the muramyl peptide which has the general formula (I):

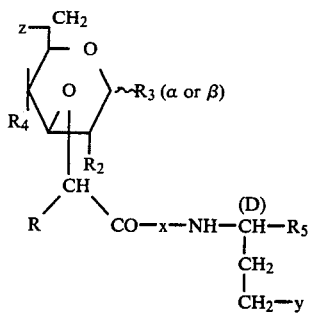

(I)

in which the following groups, when not covalently linked to the hapten, have the following meaning:

$R_5$ is a free carboxyl group or amido group, or a carboxyl group esterified by an aliphatic alcohol possessing from 1 to 10 carbon atoms, or a carboxyl group substituted by an amino acid possessing itself a free carboxyl group or an amidated group or a carboxyl group esterified by an aliphatic alcohol possessing from 1 to 10 carbon atoms, R is a hydrogen or a methyl group, $R_2$ is an acetamido or a glycoyl-amido group, $R_1$ is either —$NH_2$, or OH, or a radical comprising at the most 10 carbon atoms, corresponding to an alkyl, aryl, arylalkyl or alkylaryl group, optionally bearing hydroxyl-, amido, carboxamido-, sulfonamido-, ether, thioether, ester- or thioester substituents $R_4$ is a hydroxyl or an oxyacyl group comprising from 1 to 4 carbon atoms, X is an aminoacyl residue of the group comprising: alanyl, arginyl, asparagyl, aspartyl, cysteinyl, glutaminyl, glutamyl, glycyl, histidyl, hydroxyprolyl isoleucyl, leucyl, lysyl, methionyl, phenylalanyl, prolyl, seryl, threonyl, tryptophanyl, tyrosyl, valyl and aminobutyryl, Z is a group substituting the position at C-6 of muramic acid, and which has the following general formula (II):

$$-R_6-(R_7)_x \quad (II)$$

in which x=0 or 1 and in which,
if x=0,
$R_6$ is hydroxyl or amino and,
if x=1,
$R_6$ is hydroxyl group or amino, carboxamido, sulfonamide ether or thioether, ester or thioester,
$R_7$ then being a chain of —$CH_2$, —CH=CH—, —S—, —CO— or NH groups, —$CH_2$—; —CH=CH—, or NH-groups, said groups being optionally replaced or substituted by aryl groups or by carboxlyic, amino, sulfhydryl or hydroxyl groups, or by alkyl groups including up to 5 carbon atoms or by alkylaryl groups, arylalkyl including in all up to 8 carbon atoms or by heterocyclic groups including up to six carbon atoms and one or two oxygen, nitrogen or sulfur atoms, said alkylaryl or arylalkyl groups optionally containing carbonyl groups or being optionally substituted by carboxyl, amino, sulfhydryl or hydroxyl groups, said heterocyclic groups being themselves optionally substituted by alkyl groups which can contain up to 5 carbon atoms, carboxyl, amino, sulfhydryl or hydroxyl, the above said $R_7$ group having none the less a length not exceeding that of an n-decyl hydrocarbon chain, Y is a free or amidated carboxyl group, or an ester group comprising up to 10 carbon atoms, or substituted by an amino acid or is a group of formula (III):

$$-R_8-(R_9)_x \quad (III)$$

in which x equals 0 or 1 and
in which $R_8$ is an amide or ester linkage when x is equal to zero, or when x is different from zero, $R_8$ is a carboxamido-, ester- or thioester-group, $R_9$ then having the same meaning as $R_7$;

and which conjugate when administered in vivo elicits only antibodies or a cell mediated immunological response involving the hapten.

2. The conjugate of claim 1, wherein the hapten is a peptide or a glycopeptide.

3. The conjugate of claim 1, wherein the hapten comprises a hormone or part thereof.

4. The conjugate of claim 1 which has a molecular weight less than 3,000.

5. The conjugate of claim 4 which has a molecular weight less than 2,000.

6. The conjugate of claim 1, wherein the hapten is a peptide of less than 50 aminoacyl residues.

7. The conjugate of claim 6, wherein the hapten is a peptide of less than 30 aminoacyl residues.

8. The conjugate of claim 7, wherein the hapten is a peptide of less than 20 aminoacyl residues.

9. The conjugate of claim 1, wherein the muramyl peptide, when not conjugated with the hapten, is pyrogenic.

10. The conjugate of claim 1, wherein the hapten comprises an antigenic site which has the structure of a portion of a natural antigen.

11. The conjugate of claim 1, wherein the antigenic site is a peptide which possess a sequence present in a native peptide antigen.

12. The conjugate of claim 1, wherein the hapten comprises at least one mono- or polysaccharide.

13. The conjugate of claim 12, wherein the polysaccharide is a hexose or a pentose.

14. The conjugate of claim 1, 11 or 12, wherein the hapten is synthetic.

15. The conjugate of claim 1, wherein X is a glycyl, seryl, valyl, leucyl, aminobutyryl residue, or alanyl.

16. The conjugate of claim 1, wherein, x being equal to zero, Z is a hydroxyl or amino function.

17. The conjugate of claim 1, wherein:
x=1,
$R_6$ is a carboxamide linkage or sulphonamide either or thioether, ester or thioester, and
$R_7$ represents one of the groups such as those indicated below
$(CH_2)_n$—COOH, particularly with n=1, 2, 3 or 4
$(CH_2)_n$—$NH_2$, particularly with n=1, 2, 3 or 4

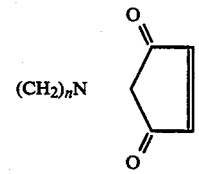

particularly with n=1, 2, 3 or 4

$(CH_2)_n-C_6H_5-NH_2$, particularly with n=0 or 1

$(CH_2)_n-SH$, particularly n=2.

18. The conjugate of claim 1, wherein the $R_5$ group is a carboxyl function esterified by an alcohol comprising from 1 to 5 carbon atoms and Y is a $-CONH_2$ group.

19. The conjugate of claim 1, wherein the group R of the muramyl-peptide group is a methyl group.

20. The conjugate of claim 1, wherein the group Z of the muramyl-peptide portion is a succinyl group.

21. The conjugate of claim 1, wherein $R_1$, $R_4$ and $R_6$ are hydroxyls and $R_2$ is acetamido, R is a methyl group, X is an alanyl group, $R_5$ is a carboxamide group or an ester group including from 1 to 5 carbon atoms, and Y is a carboxamide function.

22. The conjugate of claim 1, whrein the muramyl-peptide portion is selected from one of the following muramylpeptides:
   N-acetyl-muramyl-L-alanyl-D-isoglutamine,
   a-n.butyl-ester of N-acetyl-muramyl-L-alanyl-D-glutamine,
   6-O-succinylated derivatives of the two foregoing muramylpeptides,
   a mono-a- or y-ester or a diester of N-acetyl-muramyl-L-alanyl-D-glutamic acid, wherein ester groups contain from 1 to 5 carbon atoms.

23. The conjugate of claim 1, wherein Y includes a lysyl group.

24. The conjugate of claim 15 wherein the muramyl-peptide portion is N-acetyl-muramyl-L-alanyl-D-isoglutaminyl-L-lysine.

25. The conjugate which consists of (LH—RH-)—N—acetyl-muramyl-L-alanyl-D-isoglutamine-L-lysine.

* * * * *